US008715676B2

(12) United States Patent
Chen

(10) Patent No.: US 8,715,676 B2
(45) Date of Patent: May 6, 2014

(54) PRODUCTION AND USES OF TYPE I RIBOSOME INACTIVATING PROTEINS

(75) Inventor: Mingang Chen, Pearland, TX (US)

(73) Assignee: Bioo Scientific Corporation, Austin, TX (US)

( * ) Notice: Subject to any disclaimer, the term of this patent is extended or adjusted under 35 U.S.C. 154(b) by 284 days.

(21) Appl. No.: 12/991,319

(22) PCT Filed: Feb. 27, 2009

(86) PCT No.: PCT/US2009/035569
§ 371 (c)(1),
(2), (4) Date: Jun. 9, 2011

(87) PCT Pub. No.: WO2009/108898
PCT Pub. Date: Sep. 3, 2009

(65) Prior Publication Data
US 2011/0236366 A1     Sep. 29, 2011

Related U.S. Application Data

(60) Provisional application No. 61/031,958, filed on Feb. 27, 2008.

(51) Int. Cl.
*C07K 14/415*   (2006.01)
*C07K 19/00*    (2006.01)
*A61K 38/00*    (2006.01)

(52) U.S. Cl.
USPC ............... 424/178.1; 435/199; 435/252.3; 435/254.21; 435/320.1

(58) Field of Classification Search
None
See application file for complete search history.

(56) References Cited

U.S. PATENT DOCUMENTS 5,646,026 A        7/1997   Walsh et al.
6,680,296 B1 *     1/2004   Stirpe et al. ............... 424/134.1
2004/0266994 A1   12/2004   Stirpe et al.

FOREIGN PATENT DOCUMENTS

WO           93/09130         5/1993

OTHER PUBLICATIONS

Search Report for PCT Application No. PCT/US2009/035569 issued Nov. 26, 2009.
Written Opinion for PCT Application No. PCT/US2009/035569 issued Nov. 26, 2009.
International Preliminary Report on Patentability for PCT Application No. PCT/US2009/035569 issued Jun. 17, 2010.
Xia et al. "Purification and characterization of Moschatin, a novel type I ribosome-inactivating protein from the mature seeds of pumpkin (*Cucurbita moschata*), and preparation of its immunotoxin against human melanoma cells" Cell Research (2003); 13(5):369-374.
Chen et al. "Crystallization and preliminary crystallographic study of cucurmosin, a ribosome-inactivating protein from the sarcocarp of *Cucurbita moschata*" Acta Cryst. (2000). D56, 665-666.
Barbieri et al. "Ribosome-inactivating proteins in edible plants and purification and characterization of a new ribosome-inactivating protein from *Cucurbita moschata*" Biochimica et Biophysica Acta 1760 (2006) 783-792.

* cited by examiner

*Primary Examiner* — Kagnew H Gebreyesus
(74) *Attorney, Agent, or Firm* — Meyertons, Hood, Kivlin, Kowert & Goetzel, P.C.; Eric B. Meyertons

(57) ABSTRACT

Described herein are methods to express and purify recombinant type 1 ribosome inactivating proteins. Included are methods for using recombinant cucurmosin as a therapeutic to treat cancer and infectious diseases.

5 Claims, 1 Drawing Sheet

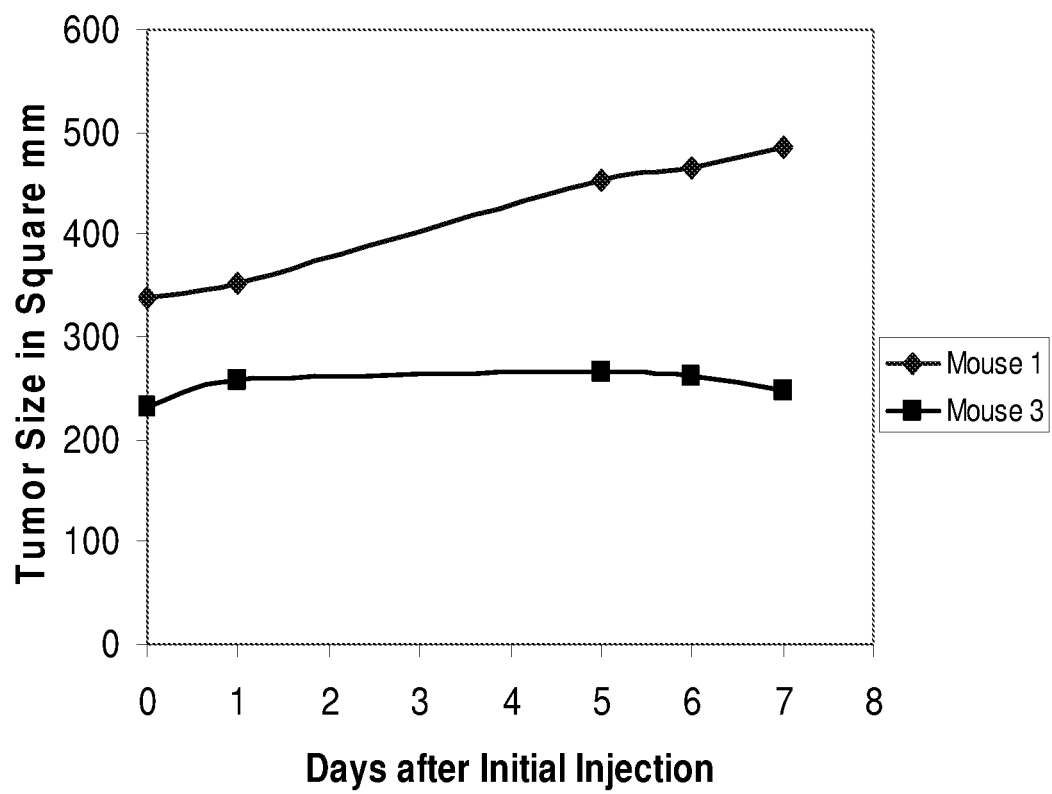

SEQUENCE LISTING

```
<160> NUMBER OF SEQ ID NOS: 5

<210> SEQ ID NO 1
<211> LENGTH: 1178
<212> TYPE: DNA
<213> ORGANISM: Cucurbita moschata

<400> SEQUENCE: 1
gagattttta gaaaaaaaaa ccaaatggtt tcggggatca acactgcgtt tgctggcttt      60
gatgaaaatc caaacccatc aactgaaaaa gatgaacaaa tccttagccc tttcgtttct     120
atttctcacc atcttcctca acactcgtcc cgctgatgcc aatgtgcgtt tcgatttgtc     180
cagtgccaca agctcatctt acaaaacttt tataaaaaat ttgagggaag cacttccaaa     240
ggatgggaaa gtgtatgaca ttcctgtgtt actttcgact gtaatggact cgaggcgctt     300
catactaata gatctcgtca attacgacgg tcaatccatc acagctgcca tagatgtgct     360
aaacgtatat atcgtggcat acagcacagg cacagtgtcc tactttttttc agcaagttcc     420 agctcaagct cccaaattgc tgttcaaagg cactcagcaa aggacacttc catacacagg     480
taattacgag aaccttcaaa ctgctgcaaa aaagctaaga gaaacatcg agcttggact     540 cccagctcta gacagtgcca ttaccacctt gtttcattac aacgccgagg ctgctgcttc     600
agcgctgctc gttctcattc aaacgacctc tgaagctgca aggtttagat atatcgagct     660
acagattgct aacaatgttg ggacgaaatt taagccaagt caaacgatca taagcttgga     720
aaacaactgg tctgcgctct ccaaacaaat ccaaattgcc aagaacaaaa atgggcaatt     780
tgaaactcca gttatcctta tagaccctca aggaaatcgt gttcaaataa caaacgtgac     840
ttcgaacgtt gtaacccaaa acatcaagct gctgctgaac attggtgcaa cagttgatac     900
aatggccgcc aacgacgatg tggatgagat gacgagcggt gttcccataa ggctatcaag     960
ctgtggccat gagatggaaa ggaagtcagt ggagaatggc cggcatgcaa attatgtatc    1020
ggtgtaactt ttgaagttac aggtatagtg ggtattaaga ctttagtagt ccacccacag    1080
aaataaggca tgtgttcatt gtgtttatgt gttttatttc ttaaatgcta aataaaatgg    1140
aacgatgaag tccctatgac aaaaaaaaaa aaaaaaaa                            1178

<210> SEQ ID NO 2
<211> LENGTH: 311
<212> TYPE: PRT
<213> ORGANISM: Cucurbita moschata
```

-continued

<400> SEQUENCE: 2

Met Asn Lys Ser Leu Ala Leu Ser Phe Leu Phe Leu Thr Ile Phe Leu
1               5                   10                  15

Asn Thr Arg Pro Ala Asp Ala Asn Val Arg Phe Asp Leu Ser Ser Ala
            20                  25                  30

Thr Ser Ser Ser Tyr Lys Thr Phe Ile Lys Asn Leu Arg Glu Ala Leu
        35                  40                  45

Pro Lys Asp Gly Lys Val Tyr Asp Ile Pro Val Leu Leu Ser Thr Val
    50                  55                  60

Met Asp Ser Arg Arg Phe Ile Leu Ile Asp Leu Val Asn Tyr Asp Gly
65                  70                  75                  80

Gln Ser Ile Thr Ala Ala Ile Asp Val Leu Asn Val Tyr Ile Val Ala
                85                  90                  95

Tyr Ser Thr Gly Thr Val Ser Tyr Phe Phe Gln Val Pro Ala Gln
            100                 105                 110

Ala Pro Lys Leu Leu Phe Lys Gly Thr Gln Gln Arg Thr Leu Pro Tyr
        115                 120                 125

Thr Gly Asn Tyr Glu Asn Leu Gln Thr Ala Ala Lys Lys Leu Arg Glu
    130                 135                 140

Asn Ile Glu Leu Gly Leu Pro Ala Leu Asp Ser Ala Ile Thr Thr Leu
145                 150                 155                 160

Phe His Tyr Asn Ala Glu Ala Ala Ser Ala Leu Leu Val Leu Ile
                165                 170                 175

Gln Thr Thr Ser Glu Ala Ala Arg Phe Arg Tyr Ile Glu Leu Gln Ile
            180                 185                 190

Ala Asn Asn Val Gly Thr Lys Phe Lys Pro Ser Gln Thr Ile Ile Ser
        195                 200                 205

Leu Glu Asn Asn Trp Ser Ala Leu Ser Lys Gln Ile Gln Ile Ala Lys
    210                 215                 220

Asn Lys Asn Gly Gln Phe Glu Thr Pro Val Ile Leu Ile Asp Pro Gln
225                 230                 235                 240

Gly Asn Arg Val Gln Ile Thr Asn Val Thr Ser Asn Val Val Thr Gln
                245                 250                 255

Asn Ile Lys Leu Leu Leu Asn Ile Gly Ala Thr Val Asp Thr Met Ala
            260                 265                 270

Ala Asn Asp Val Asp Glu Met Thr Ser Gly Val Pro Ile Arg Leu
        275                 280                 285

Ser Ser Cys Gly His Glu Met Glu Arg Lys Ser Val Glu Asn Gly Arg
    290                 295                 300

His Ala Asn Tyr Val Ser Val
305                 310

<210> SEQ ID NO 3
<211> LENGTH: 1094
<212> TYPE: DNA
<213> ORGANISM: Cucurbita moschata

<400> SEQUENCE: 3
ttaatacgac tcactatagg ggaattgtga gcggataaca attcccctct agaaataatt    60 tgtttaact ttaagaagga gatatacata tgaacgtgcg ttttgatctg agcagcgcga    120
cctctagtag ctataaaacc tttattaaaa acctgcgtga agcgctgccg aaagatggca    180
aagtgtatga tattccggtg ctgctgagca ccgtgatgga tagccgtcgt tttattctga    240
ttgatctggt gaactatgat ggccagagca ttaccgcggc gattgatgtg ctgaacgtgt    300

-continued

```
atattgtggc gtatagcacc ggcaccgtga gctacttttt ccagcaggtg ccggcgcagg    360
cgccgaaact gctgtttaaa ggcacccagc agcgtaccct gccgtatacc ggcaactatg    420
aaaacctgca gaccgcggcg aaaaaactgc gtgaaaacat tgaactgggc ctgccggcgc    480
tggatagcgc gattaccacc ctgtttcatt ataacgcaga agcagcagca agcgcactgc    540
tggtgctgat tcagaccacc agcgaagcag cacgttttcg ttatattgaa ctgcagattg    600
cgaacaacgt gggcaccaaa tttaaaccga gccagaccat tattagcctg aaaacaact    660 ggagcgcgct gagcaaacag attcagattg cgaaaaacaa aaacggccag tttgaaaccc    720
cggtgattct gattgatccg cagggcaacc gtgtgcagat taccaacgtg accagcaacg    780
tggtgaccca gaacattaaa ctgctgctga acattggcgc gaccgtggat accatggcgg    840
cgaacgatga tgtggatgaa atgaccagcg gcgtgccgat tcgtctgagc agctgcggcc    900
atgaaatgga acgtaaaagc gtggaaaacg gccgtcatgc gaactatgtg agcgtgctcg    960
agcaccacca ccaccaccac tgagatccgg ctgctaacaa agcccgaaag gaagctgagt   1020
tggctgctgc caccgctgag caataactag cataacccct tggggcctct aaacgggtct   1080
tgagggtttt tttg                                                    1094
```

<210> SEQ ID NO 4
<211> LENGTH: 297
<212> TYPE: PRT
<213> ORGANISM: Cucurbita moschata

<400> SEQUENCE: 4

```
Met Asn Val Arg Phe Asp Leu Ser Ser Ala Thr Ser Ser Ser Tyr Lys
1               5                   10                  15

Thr Phe Ile Lys Asn Leu Arg Glu Ala Leu Pro Lys Asp Gly Lys Val
            20                  25                  30

Tyr Asp Ile Pro Val Leu Leu Ser Thr Val Met Asp Ser Arg Arg Phe
        35                  40                  45

Ile Leu Ile Asp Leu Val Asn Tyr Asp Gly Gln Ser Ile Thr Ala Ala
    50                  55                  60

Ile Asp Val Leu Asn Val Tyr Ile Val Ala Tyr Ser Thr Gly Thr Val
65                  70                  75                  80

Ser Tyr Phe Phe Gln Gln Val Pro Ala Gln Ala Pro Lys Leu Leu Phe
                85                  90                  95

Lys Gly Thr Gln Gln Arg Thr Leu Pro Tyr Thr Gly Asn Tyr Glu Asn
            100                 105                 110

Leu Gln Thr Ala Ala Lys Lys Leu Arg Glu Asn Ile Glu Leu Gly Leu
        115                 120                 125

Pro Ala Leu Asp Ser Ala Ile Thr Thr Leu Phe His Tyr Asn Ala Glu
    130                 135                 140

Ala Ala Ala Ser Ala Leu Leu Val Leu Ile Gln Thr Thr Ser Glu Ala
145                 150                 155                 160

Ala Arg Phe Arg Tyr Ile Glu Leu Gln Ile Ala Asn Asn Val Gly Thr
                165                 170                 175

Lys Phe Lys Pro Ser Gln Thr Ile Ile Ser Leu Glu Asn Asn Trp Ser
            180                 185                 190

Ala Leu Ser Lys Gln Ile Gln Ile Ala Lys Asn Lys Asn Gly Gln Phe
        195                 200                 205

Glu Thr Pro Val Ile Leu Ile Asp Pro Gln Gly Asn Arg Val Gln Ile
    210                 215                 220

Thr Asn Val Thr Ser Asn Val Val Thr Gln Asn Ile Lys Leu Leu Leu
225                 230                 235                 240
```

```
Asn Ile Gly Ala Thr Val Asp Thr Met Ala Ala Asn Asp Val Asp
            245                 250                 255

Glu Met Thr Ser Gly Val Pro Ile Arg Leu Ser Ser Cys Gly His Glu
        260                 265                 270

Met Glu Arg Lys Ser Val Glu Asn Gly Arg His Ala Asn Tyr Val Ser
    275                 280                 285

Val Leu Glu His His His His His His
    290                 295

<210> SEQ ID NO 5
<211> LENGTH: 245
<212> TYPE: PRT
<213> ORGANISM: Cucurbita moschata

<400> SEQUENCE: 5

Asn Val Arg Phe Asp Leu Ser Ser Ala Thr Ser Ser Ser Tyr Lys Thr
1               5                   10                  15

Phe Ile Lys Asn Leu Arg Glu Ala Leu Pro Lys Asp Gly Lys Val Tyr
            20                  25                  30

Asp Ile Pro Val Leu Leu Ser Thr Val Met Asp Ser Arg Arg Phe Ile
        35                  40                  45

Leu Ile Asp Leu Val Asn Tyr Asp Gly Gln Ser Ile Thr Ala Ala Ile
    50                  55                  60

Asp Val Leu Asn Val Tyr Ile Val Ala Tyr Ser Thr Gly Thr Val Ser
65                  70                  75                  80

Tyr Phe Phe Gln Gln Val Pro Ala Gln Ala Pro Lys Leu Leu Phe Lys
                85                  90                  95

Gly Thr Gln Gln Arg Thr Leu Pro Tyr Thr Gly Asn Tyr Glu Asn Leu
            100                 105                 110

Gln Thr Ala Ala Lys Lys Leu Arg Glu Asn Ile Glu Leu Gly Leu Pro
        115                 120                 125

Ala Leu Asp Ser Ala Ile Thr Thr Leu Phe His Tyr Asn Ala Glu Ala
    130                 135                 140

Ala Ala Ser Ala Leu Leu Val Leu Ile Gln Thr Thr Ser Glu Ala Ala
145                 150                 155                 160

Arg Phe Arg Tyr Ile Glu Leu Gln Ile Ala Asn Asn Val Gly Thr Lys
                165                 170                 175

Phe Lys Pro Ser Gln Thr Ile Ile Ser Leu Glu Asn Asn Trp Ser Ala
            180                 185                 190

Leu Ser Lys Gln Ile Gln Ile Ala Lys Asn Lys Asn Gly Gln Phe Glu
        195                 200                 205

Thr Pro Val Ile Leu Ile Asp Pro Gln Gly Asn Arg Val Gln Ile Thr
    210                 215                 220

Asn Val Thr Ser Asn Val Val Thr Gln Asn Ile Gln Leu Leu Leu Asn
225                 230                 235                 240

Ile Gly Ala Thr Ala
                245
```

US 8,715,676 B2

PRODUCTION AND USES OF TYPE I RIBOSOME INACTIVATING PROTEINS

PRIORITY CLAIM

This application is a 371 of PCT Application PCT/US2009/035569, filed Feb. 27, 2009, which claims priority to U.S. Provisional Application Ser. No. 61/031,958, filed Feb. 27, 2008.

BACKGROUND OF THE INVENTION

1. Field of the Invention

The present disclosure generally relates to the production and/or therapeutic use of recombinant type 1 ribosome inhibiting proteins for the treatment of cancer and infectious diseases.

2. Description of the Relevant Art

Ribosome Inactivating Proteins (RIPs), found widely among plants, have been used for their medicinal properties since ancient times. Cucurmosin is an example of a Type 1 RIP. Type 1 RIPs are monomers of about 30 kilodalton (kDa) whereas Type 2 RIPs are heterodimers. Type 1 RIPs tend to have less toxicity than the Type 2 RIPs for normal cells. Cucurmosin is isolated from *Cucurbita moschata* (pumpkin) seeds—something that is naturally consumed by humans, suggesting a low innate toxicity. Cucurmosin has selective toxicity for tumor cells compared to non-cancer cells in culture via the induction of apoptosis. RIPs such as cucurmosin have therapeutic potential for diseases in addition to cancers including use as an antiviral agent and an antifungal agent.

RIPs are a large family of proteins, generally present in one or more tissues of individual plants. They can be divided into three families based on the number and organization of protein subunits. Type I RIPs (>60 members) contain a single chain of 26-31 kDa. Type II RIPs (~15 cloned members), which include the relatively well-known ricin compound, possess two disulfide-linked chains—an enzymatic A chain and a lectinic B chain enabling the protein to effectively interact with a broad range of cell types. Type III RIPs are an alternative, non-classical group that are much less characterized than type I or II versions and contain either internal repressive peptides or additional protein chains of unknown function. RIP expression in its natural host is generally stimulated by a variety of environmental stresses upon the plant, including viral infection. Expression is often observed during cell senescence. These observations suggest that RIPs are part of an innate defense mechanism of plants to ensure appropriate cell growth, a hypothesis that emphasizes their potential as possible anti-tumor and anti-infectious disease drugs in humans.

RIPs inhibit protein synthesis. Through interactions with a variety of ribosomal proteins, RIPs target the ribosome where they specifically act as an N-glycosidase and remove adenosine 4324 from the conserved 'sarcin/ricin' loop in 28S ribosomal RNA (rRNA). In addition to this rRNA cleavage activity, several other enzymatic activities have been associated with RIPs. RIPs can specifically remove adenine from the ADP-ribose chain of the Poly (ADP-ribose) Polymerase (PARP) protein, a factor involved in DNA repair. Two RIPs have also been implicated in DNA damage, suggesting caspase activation leading to apoptosis. Some RIPs have been associated with glycosidase-independent nuclease activities as well as superoxide dismutase/antioxidant activity. Interaction with the 5' cap of mRNAs has been reported which is of importance since the eukaryotic cap binding protein eIF4E may transform cells, and translational defects associated with such transformations are often associated with certain cancers (e.g., breast cancers). In summary, although their rRNA modification activity is best characterized, RIPs appear to have additional activities in cells contributing to their biological effects.

RIPs may protect plants from a variety of infectious diseases (e.g., viruses). Introducing the RIP genes into commercially relevant crops may provide protection against some of these diseases.

SUMMARY OF THE INVENTION

In some embodiments, a method for preparing substantially purified recombinant type 1 ribosome inactivating protein (RIP) may include obtaining a protein sequence. The protein sequence may include at least a portion of a recombinant type 1 RIP. The method may include synthesizing a nucleic acid encoding the type 1 RIP using a gene sequence optimized for use in the host cell to express the type 1 RIP. The method may include cloning the nucleic acid into an appropriate expression vector. The method may include transferring the expression vector to an appropriate protein expression system. The method may include inducing the expression of the recombinant type 1 RIP. In some embodiments, the method may include substantially purifying the expressed recombinant type 1 RIP.

In some embodiments, the recombinant type 1 RIP may be used to treat cancer and/or an infectious disease including administering to an individual who would benefit from such treatment an effective amount of a composition. The composition may include recombinant type 1 RIP, and/or functional derivatives thereof.

In some embodiments, a pharmaceutical composition may be suitable for use in the treatment of cancer. The pharmaceutical composition may include an effective amount of natural cucurmosin, recombinant cucurmosin, and/or functional derivatives thereof. The pharmaceutical composition may include an appropriate pharmaceutical carrier medium. In some embodiments, a derivative of recombinant cucurmosin may include one or more of a ligand conjugated to cucurmosin, a truncated cucurmosin polypeptide, and/or a cucurmosin polypeptide. The cucurmosin polypeptide may include at least one mutation in the polypeptide sequence thereof.

In some embodiments, a method of inducing apoptosis in cancer cells may include contacting cancer cells with an at least partially purified preparation of recombinant cucurmosin, and/or a functional derivative thereof.

In some embodiments, a method for preparing substantially purified recombinant cucurmosin may include obtaining a nucleic acid sequence. The nucleic acid sequence may include at least a portion of cucurmosin. The method may include cloning the nucleic acid into the appropriate expression vector. The method may include transferring the expression vector to an appropriate protein expression system. The method may include inducing the expression of the recombinant cucurmosin. The method may include substantially purifying the expressed recombinant cucurmosin.

BRIEF DESCRIPTION OF THE DRAWINGS

Other objects and advantages of the invention will become apparent upon reading the following detailed description and upon reference to the accompanying drawings in which:

FIG. 1 depicts a graph of the results of treating HMEL tumors in mice with recombinant cucurmosin by tail vein injection.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

In some embodiments, a method of preparing at least partially purified recombinant type 1 RIP, and/or a functional derivative thereof is provided. The method may include obtaining an expression vector containing at least a portion of the type 1 RIP open reading frame (ORF) having an optimized gene sequence and introducing the expression vector in an appropriate host cell. The method may include isolating the recombinant protein expressed by the host cells.

In some embodiments, a method of preparing at least partially purified, recombinant cucurmosin is provided. The method may include obtaining an expression vector containing at least a portion of the cucurmosin ORF sequence and introducing the expression vector in an appropriate host cell. The method may further include isolating the recombinant protein expressed by the host cells.

"Type 1 Ribosome Inactivating Proteins" (RIPs), as used herein, generally are a family of proteins from the plant kingdom that are cytotoxic enzymes. RIPs may be polynucleotide adenosines glycosidases that cleave at the conserved sequence GAGA at the glycosidic bond of eukaryotic ribosomes in the α-sarcin/ricin (S/R) loop. In general, type 1 RIPs may depurinate both eukaryotic and prokaryotic ribosomal RNA (rRNA) in the presence or absence of the ribosomal proteins. However, not all type 1 RIPs depurinate all prokaryotic rRNA. Those type 1 RIP that are active against *E. coli* rRNA, may cleave a bond between A-2660 and the ribose of the 23S rRNA. The depurination of the rRNA inactivates the ribosome and inhibits protein synthesis in the cell. Type 1 RIPs also may depurinate DNA, poly (A), viral RNA and mRNA.

Type 1 RIPs isolated from their natural plant sources may include single chain polypeptides with a molecular weight of about 30 kilodalton (kDa). Type 1 RIPs may be expressed in a prepro-form, having an N-terminal signal sequence (pre-) and a C-terminal sequence (pro-). These sequences may be cleaved to generate the mature protein. Type 1 RIPs may include, but are not limited to, cucurmosin, moschatin, ME1 tricosanthin, dianthin, bouganin, bryodin, gelonin, pokeweed antiviral protein (PAP), saporin, sechiumin, momorcharin, luffin, CAP30, trichoanguin, beetin, karasurin-A, clavin, and lychnin.

In some embodiments, a type 1 RIP may be a derivative of the type 1 RIP. In an embodiment, it may be a prepro-RIP. In an embodiment, it may be a pre-RIP. In an embodiment, it may be a pro-RIP. Any of these derivatives may be expressed with an affinity handle (i.e., a tag) to simplify purification. In one embodiment, the type 1 RIP may comprise a poly histidine sequence at the amino- or carboxy-termini. Other tags that may be used to purify the type 1 RIP include glutathione S-transferase (GST), biotin, etc. In an embodiment, the type 1 RIP may comprise a maltose binding protein at the amino- or carboxy-termini. One skilled in the art realizes there are many other affinity handles that may be useful. After attachment of the affinity handle, the resulting tagged type 1 RIP may be passed through an affinity column and purified. The tag may be cleaved off the type-1 Rip after purification using known methods for decoupling.

In some embodiments, a type 1 RIP may include the non-glycosylated form of the RIP protein (e.g., the protein (cucurmosin), a type I RIP from the Sarcocarp of *Cucurbita Moschata*, see SEQUENCE ID NO:5 herein below). Post-translational modifications in the structure of the type-1 RIP may be made. For example, sugar moieties (e.g., N-acetyl-D-glucosamine; beta-D-mannose; alpha-D-mannose, and xylopyranose) may be linked together in a chain and attached to the side chain of Asparagine 225 (in the middle of the VQITNVTSNV sequence).

In one embodiment, there may be one or more amino acid substitutions in the type 1 RIP sequence compared to the protein isolated from its natural source or compared to the protein sequence translated from the cDNA. In an embodiment, there may be amino acid deletions or additions to the type 1 RIP compared to the protein isolated from its natural source or compared to the protein sequence translated from the cDNA.

In one embodiment, the type 1 RIP may be a mutant that is non-lethal to *E. coli* but is cytotoxic to mammalian cells.

"Host cell", as used herein, generally refers to the cell in which the recombinant protein is expressed. The host cell may be of prokaryotic origin, yeast, a plant, insect cells and/or mammalian cells. In one embodiment, the host cell may be *Escherichia coli* (*E. coli*). In an embodiment, the host cell may be *E. coli* BL21 (DE3) pLys S. In one embodiment, the yeast may be of the genus *Pichia*. In an embodiment, the insect cells may include Sf9 cells. In an embodiment, the host cell may include a tobacco plant. In an embodiment, the host cell may be *Nicotiana tabacum*.

In one embodiment, the host cell may be an *E. coli* strain comprising mutant ribosomes that are not inactivated by the type 1 RIP. In an embodiment, type 1 RIP which are usually toxic to *E. coli* may be expressed in these *E. coli*.

"Gene optimization", as used herein, generally refers to the process of generating a gene sequence that will yield optimal quantities of the gene product in the host cell. One skilled in the art realizes that there are many algorithms available to perform the optimization. The Optimum Gene™ algorithm is provided by GenScript Corp. (Piscataway, N.J.). The algorithms consider factors including, but not limited to, codon usage bias, mRNA structure, GC content, promoter sequences and termination sequences for the intended host cell.

"Ligands", as used herein, generally refers to molecules that bind specifically to a cell surface. Usually, the ligand binds specifically to cell receptors. Ligands include, but are not limited to proteins, glycoproteins, carbohydrates, aptamers or lipids.

In one embodiment, the ligand may include a monoclonal antibody (MAB). A MAB may be isolated from ascites fluid from an animal (e.g., mouse or rat). A MAB may be isolated from the supernatant of cells grown in culture. The MAB used as a ligand may be of the IgG subclass but may also be an IgM, IgE or IgA. Usually, an IgG MAB is affinity purified using protein A or G sepharose. In other instances, the MAB may be isolated by salt fractionation. MABs are commercially available from a variety of vendors. In some embodiments, the MAB is selected based on its ability to recognize the native structure of the cell receptor. In many instances, a MAB recognizes only a denatured form of the cell receptor and is useful for applications such as immunoblotting or fixed immunofluorescence assays (IFA). In some embodiments, a MAB will most likely be functional if it functions in immunoprecipitations or non-fixed IFA.

In one embodiment, the ligand is a derivative of a MAB containing the complementary-determining region (CDR) or antigen binding site. In some aspects, the MAB fragment may be a recombinant protein. One skilled in the art will appreciate that there are several methods to generate and modify a MAB. In some embodiments, the MAB fragment is recombinantly expressed and purified as a single chain fragment variable (scFv). In some embodiments, the recombinant MAB may be genetically manipulated to be more amenable to carrier conjugation. In some embodiments, a MAB may be digested with proteases to generate fragments of the MAB (Fab) that may bind to the antigen. In an embodiment, the carbohydrate residues of the MAB may be treated chemically or enzymatically to be more amenable to carrier conjugation.

In an embodiment, the ligand may be a polyclonal antibody. The IgG fraction may be isolated from serum. In these instances, the Fc portion of the IgG may be recognized by the Fc receptors on cells like macrophages.

In an embodiment, the ligand is the natural ligand of the cell receptor. Natural ligands may include peptide hormones (e.g., insulin), growth factors (e.g., epidermal growth factor), small molecules (e.g., folate), proteins and/or glycoproteins (eg. orosomucoid). The ligand may be a derivative of the natural ligand (e.g., a fragment of the ligand which binds to the cell receptor). In an embodiment, the ligand may include a recombinant protein of the natural ligand.

In an embodiment, the natural ligand may be modified. For example, orosomucoid, a glycoprotein recognized by liver cell, has its terminal sialic acid residues removed by mild acid hydrolysis to form asialoorosomucoid.

"Immunoconjugate", as used herein, generally refer to a type 1 RIP associated with a ligand.

In one embodiment, the association may be through a chemical reaction using cross-linking reagents. In one embodiment, the cross-linking agents may be hetero-bifunctional having functional groups including but not limited to, aryl azides, carbodiimide, hydrazine, imidoester, isocynate, maleimide, N-hydroxysuccinimide (NHS)-ester and sulfo-NHS-ester. The bonds they produce may include, but are not limited to, amide, disulfide, hydrazone and ester bonds.

Examples of cross-linking agents include, but are not limited to, succinimidyl 4-formylbenzoate (SFB), succinimidyl 4-hydrazinonicotinate acetone hydrazone (SANH), 1-ethyl-3-[3-dimethylaminopropyl]carbodiimide (EDC), N-succinimidyl 3-(2-pyridyldithio)-propionate (SPDP), 2-Iminothiolane (Traut's Reagent), SATA, and 3-[2-pyridyldithio] propionyl hydrazide (PDPH).

In one embodiment, SFB is reacted with free primary amine groups of the type 1 RIP while introducing reactive aldehyde groups. SANH is reacted with free primary amines of the ligand while introducing reactive hydrazine groups. The SFB activated-type 1 RIP is mixed with the SANH activated-ligand. The reactive aldehyde groups react with the hydrazine groups to generate hydrazone bonds, thus producing the immunoconjugate.

In one embodiment, the association of the ligand and the type 1 RIP may be through genetic manipulation to generate a fusion protein. The ligand may be fused to the ligand at the amino- or carboxy-termini. In one embodiment, the gene sequence of the fusion protein is optimized for expression in its host cell.

In an embodiment, a method of treating of cancer or infectious diseases may include administering to an individual who would benefit from such treatment an effective amount of a composition comprising recombinant type 1 RIP or cucurmosin, and/or functional derivatives thereof.

In an embodiment, a method of protecting plants from infectious diseases may include introducing a type 1 RIP or cucurmosin gene or a portion thereof with optimized codon sequences, to plants of interest wherein the gene product is expressed in the plants.

In an embodiment, a pharmaceutical composition suitable for use in the treatment of cancer may include an effective amount of recombinant type 1 RIP or cucurmosin, or functional derivatives thereof in combination with an appropriate pharmaceutical carrier medium. In one embodiment, these proteins are expressed using optimized codon sequences.

In an embodiment, a derivative of recombinant type 1 RIP or cucurmosin may include an immunotoxin conjugated to cucurmosin, a truncated cucurmosin polypeptide, and/or a cucurmosin polypeptide including at least one mutation in the polypeptide sequence thereof.

In an embodiment, an isolated nucleic acid sequence may encode a derivative of a type 1 RIP, a truncated type 1 RIP polypeptide, and/or a type 1 RIP polypeptide including at least one mutation in the polypeptide sequence thereof. The nucleic acid sequence may include codons optimized for the host cell.

In an embodiment, an isolated nucleic acid sequence may encode a derivative of cucurmosin, a truncated cucurmosin polypeptide, and/or a cucurmosin polypeptide including at least one mutation in the polypeptide sequence thereof. In an embodiment, the nucleic acid sequence may include codons optimized for the host cell.

In an embodiment, a method of killing cancer cells may include contacting cancer cells with an at least partially purified preparation of recombinant cucurmosin, and/or a functional derivative thereof.

In an embodiment, a method may include introducing a nucleic acid sequence encoding a derivative of cucurmosin into cells which are introduced into individuals, such that the cells carrying the cucurmosin nucleic acid produce an effective amount of cucurmosin polypeptide to the benefit of the individual.

It is contemplated that the RIPs disclosed herein and produced by the methods disclosed herein may be used in the following applications without limitation: as an antiparasitic; as an abortifacient, for removal of cells from culture; as an anti-inflammatory; as an anti-spasm; as an analgesic; in ophthalmology treatments, for agricultural applications, and for veterinary applications.

In another embodiment, it is contemplated that antibodies may be produced that are specific to type I RIP. Such antibodies may be used for the detection of the RIP for which it was generated. Additionally, the produced antibodies may be used for the purification of the RIP using, for example, affinity matrix after binding to the RIP.

In another embodiment, engineered organisms may be produced that include a tagged type 1 RIP disclosed herein and produced by the methods disclosed herein, and its derivatives. Such engineered organisms may be used, for example, to overexpress the type I RIP to treat cancer or other diseases.

EXAMPLES

Having now described the invention, the same will be more readily understood through reference to the following example(s), which are provided by way of illustration, and are not intended to be limiting of the present invention. Although methods and materials similar or equivalent to those described herein may be used in the application or testing of the present embodiments, suitable methods and materials are described below.

Example 1

Cloning and Sequencing of Cucurmosin cDNA

Total RNA was isolated from *Cucurbita* moschata leaves. The leaves were frozen and then ground. The powdered leaves were added to 1 ml of TRIzol (Invitrogen) and disrupted using a glass homogenizer. The insoluble material was removed by centrifugation. The soluble phase was mixed with chloroform, incubated at 21° C. for 2 minutes and then centrifuged for 15 minutes at 12,000 rpm. The upper aqueous phase was removed, mixed with isopropanol and centrifuged. The RNA pellet was washed with 75% ethanol and then solubilized in 75 µl of Elution Solution (Ambion, RNAqueous Kit #AM1912).

Using previously published protein and DNA sequences for cucurmosin, oligonucleotide primers were designed to synthesize cucurmosin cDNA from the *C. moschata* total RNA. According to the manufacturer's instructions, the FirstChoice® RLM-Race kit (Ambion, #AM1700) was used to generate PCR products of the extreme 5' and 3' termini of the cucurmosin mRNA. The PCR products were sequenced and the full-length cDNA sequence established (Seq. ID 1) and the protein sequenced translated (Seq. ID 2). Based on N-terminal sequencing data and X-ray crystal structures of the mature protein, cucurmosin is deduced as a 245 amino acid protein, consistent with the data of other type 1 RIPs (Seq ID 5). On the other hand, our protein (Seq. ID 2) has a 23 amino acid signal sequence (pre-sequence) at the N-terminus and a 44 amino acid extrapeptide (pro-sequence) at the C-terminus. This cloning approach enabled us to identify the additional 44 amino acids on the seat C terminus and 23 amino acids on the N terminus of cucurmosin which may be critical for its activity.

Example 2

Expressing Cucurmosin in *E. Coli* Using the pUC57 Vector

To potentially produce the highest level of cucurmosin expression in *E. coli*, the protein sequence to be expressed was given to GenScript Corp. (Piscataway, N.J.) to synthesize a cucurmosin gene optimized for expression in *E. coli*. GenScript Corp. has an OptimumGene™ algorithm that takes into consideration a variety of critical factors involved in different stages of protein expression such as codon adaptability, GC content and mRNA structure. In this example, the pro-cucurmosin was synthesized with a 5' T7 promoter and a C-terminal histidine tag (Seq. ID 3) and cloned into the EcoRV site of the pUC 57 vector (GenScript, #SD1176). The gene sequence translated to a protein of 297 amino acids (SEQ ID 4).

The recombinant plasmid, pUC57-RIP, was transformed into *E. coli* BL21 (DE3) pLysS. DE3 is a prophage carrying T7 RNA polymerase and lacI$^q$. Transformed plasmids with T7 promoters are repressed until isopropyl β-D-thiogalactoside (IPTG) is added to the culture. The pLysS produces T7 lysozyme, is a muramidase that cleaves (hydrolyzes) proteoglycan. Using this system, leaky recombinant protein expression is minimized until IPTG is added.

The pUC57-RIP clones were grown in Rich Induction Medium (20 g/L Tryptone, 10 g/L Yeast extract, 5 g/L NaCl, 1.2 mL/L of 5N NaOH, 1% glucose, 100 µg/mL Ampicillin, and Chloramphenicol). The cells were grown with shaking at 37° C. until they reached an A600 of 0.56. An aliquot of the uninduced cells was taken, centrifuged and the cell pellet frozen for later analysis.

Half of the remaining culture was grown at 25° C. and the other half at 37° C. with shaking. IPTG was added to 0.8 mM to both cultures and grown for 3 hours and ~18 hours. At these times, cells were harvested and the cells were pelleted by centrifugation and frozen at −20° C.

All pelleted cells were lysed in 1/20 the volume of the original culture volume in lysis buffer (40 mM Tris-Cl pH 7.5, 0.5% Triton X-100, 0.5 mg/mL lysozyme, 0.01 M NaCl). The pellets were vortexed until the lysate was to viscous to pipet. At that point, benzonase (2-4 µl per liter of culture) was added and incubated on ice until the sample became freely flowing (i.e., less viscous). The samples were superfuged in a Sorvall superfuge at 10° C. for 40 min. The supernatants were moved to fresh tubes and the pellets were resuspended with an equal volume of buffer. The samples were analyzed by SDS-PAGE and immunoblotted. The samples were transferred from the SDS-PAGE gel to PVDF paper and then probed with an anti-his tag antibody. The pro-cucurmosin was detected primarily in the cells grown at 25° C. having an apparent molecular weight of 38 kDa. The apparent molecular weight of the recombinant RIP is larger than that of the native plant protein; this is probably due to its longer C-terminal amino acid sequence discovered through our cloning process described in Example 1. In addition, the cells grown for ~18 hours had more pro-cucurmosin than the culture induced for 3 hours.

Example 3

Expression and Isolation of Pro-Cucurmosin in *E. Coli* Using the Pet24b Vector The pro-cucurmosin gene was sub-cloned from pUC57-RIP into pET24b. pUC57-RIP was digested with Nde I and Xho I to excise the pro-cucurmosin gene. This DNA fragment was cloned into the Nde I and Xho I site of pET24b to encode a 297 amino acid pro-cucurmosin product with a C-terminal tag of 6 histidines to mediate purification. The pET24b-RIP vector was transformed into BL21 (DE3) pLysS cells. The transformed cells were grown in one liter of Rich Induction Medium at 37° C. to an A600 of 1.0. IPTG was added to 0.8 mM and the culture was incubated at 25° C. with shaking for ~18 hours. The cells in the culture were pelleted and disrupted in 50 ml lysis buffer.

The lysate was brought to 300 mM NaCl and syringe filtered using a 0.45 µm filter. The his-tagged pro-cucurmosin was isolated using the Talon Metal Affinity Resin (ClonTech). A 1 ml Talon resin bed was washed with 5 column volumes of 100 mM NaCl: 20 mM MES pH 5.0. The column was equilibrated with 4 column volumes of wash buffer (300 mM NaCl, 50 mM sodium phosphate (monobasic) pH 8.0). The filtered lysate was passed through the column and the flow-thru saved. The column was then washed with 2 column volumes of wash buffer and 6 column volumes of wash buffer pH 7.0 (300 mM NaCl, 50 mM NaPO4 pH 7.0). Sample was eluted with 2 column volumes of 150 mM imidazole. The eluate contained a protein having the same mobility (slightly larger than the 37 kDa marker) as observed in Example 2. About 4-10 mg of protein was isolated per liter of culture.

Example 4

Cytotoxicity of Pro-Cucurmosin in Cancer Cells In Vitro

Human breast cancer cells, MDA 231 and BT 474, were grown in tissue culture to assay for the concentration at which 50% of the cells are inhibited from growing (IC50). The cells were seeded in 96-well plates at 5000 cells per well and grown overnight in RPMI 1640 supplemented with 10% fetal bovine serum and 15 µg/ml insulin. The culture medium was replaced. The recombinant cucurmosin, natural cucurmosin and vinblastine were added to the cells at various concentrations. Likewise, the non-cancer cells, LO2 and lymphocytes were treated with these drugs at different concentrations. The cells were grown for an additional 72 hours and then 20 µl of TOX8 was added to each well. The cells were incubated another 8 hours at 37° C., 5% $CO_2$ to allow time for the cells to metabolize the TOX8 indicator. Absorbance readings at 600 nm were taken of each well. Viability was indicated by a drop in absorbance at 600 nm readings.

The IC50 of recombinant cucurmosin for both cancer cell lines was just above 20 nM (TABLE 1) which was very similar to those of the natural cucurmosin and the often used cancer drug, Vinblastine. However, in contrast to Vinblastine, both the recombinant and natural cucurmosin had much higher IC50 for the non-cancer cells. These data indicate that recombinant cucurmosin may be very useful as a cancer drug since it is much more toxic to the cancer cells than the normal cells, unlike the Vinblastine.

TABLE 1

IC50 of recombinant cucurmosin.

| Cells | IC50 (nM) | | |
|---|---|---|---|
| | Recombinant Cucurmosin | Natural Cucurmosin | Vinblastine |
| TB474 | 22 | 27 | 26 |
| MDA231 | 23 | 24 | 25 |
| LO2 | 1200 | 1100 | 68 |
| Lymphocytes | 2500 | 2400 | 73 |

Example 5

Use of Pro-Cucurmosin to Reduce Tumors in Mice

Human lung cancer cells, HMEL or A549, were used to induce tumor formation in backs of NOD/SCID mice (JAX, #001303). The cells were maintained in culture. In each experiment, 5 million cells were injected into the back of the mice. Tumors formed in 2 to 3 weeks. Tumor sizes were measured using a digital caliper and then areas calculated.

In one experiment, either 5 or 50 µg recombinant cucurmosin was injected into the HMEL tumors in 100 µl of saline solution on the days that the tumors were measured. Mouse 2 had tumors in both sides of its back which were each treated separately. Over the 18 day period, the mouse injected with no cucurmosin saw its tumor increase 267% (TABLE 2). Meanwhile, tumors smaller than 40 $mm^2$ were completely abrogated using either 5 or 50 µg of cucurmosin. Mouse 3 started with the largest tumor of the group but the 5 µg treatment was able slow the tumor growth compared to the negative control.

It is also important to note that the mice did not suffer any noticeable side-effects by the cucurmosin. Mouse 1 and 3 with HMEL tumors after 18 days intratumoral treatment (Table 2), were continually administered recombinant cucurmosin by tail vein injection using 50 µg of recombinant cucurmosin in 100 µl saline solution at day 0 (the same day as day 18 of intratumoral treatment) and day 5. Seven days after initial tail vein injection with recombinant cucurmosin, the tumor size in Mouse 3 only increased 7% while the control Mouse 1 increased 43%. The cucurmosin tail vein injection resulted in no obvious toxic effects on the mice. The results of these tests are depicted in FIG. 1.

TABLE 2

Treating HMEL tumors in mice with recombinant cucurmosin, intratumorally.

| Mouse | Cucurmosin (µg) | Tumor Size ($mm^2$) | | | | | | Tumor growth (%) |
|---|---|---|---|---|---|---|---|---|
| | | Day 1 | Day 3 | Day 5 | Day 8 | Day 15 | Day 18 | |
| 1 | 0 | 92.3 | 106.7 | 137.3 | 205.1 | 251.6 | 339 | 267 |
| 2 left | 5 | 39.4 | 33 | 23 | 19.7 | 12.5 | 0 | −100 |
| 2 right | 5 | 27.8 | 24.8 | 18.5 | 12.2 | 0 | 0 | −100 |
| 3 | 5 | 162.2 | 158 | 151.8 | 186.7 | 206.7 | 231.2 | 43 |
| 4 | 50 | 23.9 | 12.2 | 9.4 | 0 | 0 | 0 | −100 |

In another group of mice, carrying tumors derived from A549 cells, 5 or 50 µg treatments of directly injected recombinant cucurmosin into the tumors was able to reduce tumors by 15 and 33%, respectively while the negative control saw the tumor grow 150% (TABLE 3).

TABLE 3

Treating A549 tumors in mice with recombinant cucurmosin, intratumorally.

| Mouse | Cucurmosin (µg) | Tumor Size ($mm^2$) | | | | | Tumor growth (%) |
|---|---|---|---|---|---|---|---|
| | | Day 1 | Day 3 | Day 5 | Day 7 | Day 9 | Day 11 |
| 1 | 0 | 47.9 | 60.6 | 70.4 | 81.9 | 98.6 | 120.2 | 150 |
| 2 | 5 | 34.7 | 38.8 | 42.4 | 40.8 | 39.5 | 29.5 | −15 |
| 3 | 50 | 100.6 | 104.1 | 108.6 | 113.1 | 78.8 | 67.3 | −33 |

Example 6

Cucurmosin as an Immunotoxin

The previous examples demonstrate that cucurmosin exhibits strong selectivity for tumor-derived cells in mice. However, cucurmosin or any other type 1 RIP may be made more specific by combining it with a targeting ligand, either chemically or through molecular manipulations. This may be important for some very refractory cancer cells that require high doses of drug for a beneficial effect to the patient. The more cell-specific the drug, the less toxicity it will induce.

Over-expression of CD44, a hyaluronan receptor, is observed in breast cancer cells and the presence of certain CD44 isoforms is emerging as an important marker of metastatic potential. Recombinant cucurmosin, may be conjugated with hyaluronan, a ligand for CD44 through chemical cross-linkers. Alternatively, it could be chemically conjugated to a monoclonal antibody (MAB) ligand or a derivative of a MAB that binds specifically to CD44. On the other hand, a protein fusion could be constructed of cucurmosin (or any other type 1 RIP) and fragment of the MAB that specifically recognizes the CD44, usually the single chain Fragment variable (scFv) region. This protein fusion may be expressed using the optimized system taught in this patent to generate high yields of immunotoxin.

The above are just a few examples of the types of immunotoxins that could be created using type 1 RIP. One skilled in the art will recognize that there are many other peptides and proteins that could be molecularly fused to cucurmosin or other type 1 RIP and expressed at high levels using codons optimized for the host in which the immunotoxin are translated. Ligands that recognize CD38, CD20, alpha-acetylcholine receptor, epidermal growth factor receptor (EGF-R), CD30, CD25, CD40, CD7 may be fused with cucurmosin. Many others may be contemplated.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A purified recombinant type 1 RIP (Ribosome Inactivating Protein) having either of amino acid sequence SEQ ID NO. 2 or SEQ ID NO. 4.

2. A pharmaceutical composition comprising a purified recombinant type 1 RIP of claim 1 and a pharmaceutical carrier medium.

3. A purified tagged type 1 RIP of claim 1 for use as a therapeutic agent.

4. A conjugate for the delivery of RIP to cells comprising:
a purified recombinant type 1 RIP having either of amino acid sequence SEQ ID NO. 2 or SEQ ID NO. 4;
a ligand, wherein the ligand is capable of binding to a surface of a cell; and
wherein the recombinant type 1 RIP and the ligand are covalently coupled to each other.

5. A conjugate for the delivery of RIP to cells comprising:
a purified recombinant type 1 RIP having either of amino acid sequence SEQ ID NO. 2 or SEQ ID NO. 4;
a ligand, wherein the ligand is capable of binding to a surface of a cell; and
wherein recombinant type 1 RIP and the ligand are a fusion protein.

* * * * *